United States Patent [19]

Kast et al.

[11] Patent Number: 5,130,453

[45] Date of Patent: Jul. 14, 1992

[54] PREPARATION OF ACYLCYCLOHEXADIONETHIOCARBOXYLIC S-ESTERS

[75] Inventors: Juergen Kast, Boehl-Iggelheim; Juergen Schubert, Mannheim; Reinhard Kaczmarek, Bobenheim, all of Fed. Rep. of Germany

[73] Assignee: BASF Aktiengesellschaft, Ludwigshafen, Fed. Rep. of Germany

[21] Appl. No.: 592,298

[22] Filed: Oct. 3, 1990

[30] Foreign Application Priority Data

Oct. 13, 1989 [DE] Fed. Rep. of Germany ....... 3934205

[51] Int. Cl.$^5$ ........................................... C07C 327/00
[52] U.S. Cl. ................... 558/251; 558/257; 558/252; 558/256; 562/26
[58] Field of Search ............... 558/251, 257, 252, 256; 562/26

[56] References Cited

U.S. PATENT DOCUMENTS 2,458,075 1/1949 Himel .................................. 558/251

FOREIGN PATENT DOCUMENTS 0125094 11/1984 European Pat. Off. ............ 558/257
293817 5/1988 European Pat. Off. ............ 558/251

OTHER PUBLICATIONS

Ber. Dt. Chem. Ges. 69 (1936) 2352.
Monatsh. Chem. 110, (1979) 759.
Houben-Weyl, Methoden der organischen Chemie, vol. 9, 753-760 (1955).
Bull. Chem. Soc. Jpn. 53, (1980), 1982.
J. Am. Chem. Soc., 93 (1971) 1419.
Angew. Chem. 89 (1977) 251.
Tetrahedron Lett. 1973, 1595.
Houben-Weyl Bd. E5*, p. 876 f, (1985).

Primary Examiner—Mary C. Lee
Assistant Examiner—Robert C. Whittenbaugh
Attorney, Agent, or Firm—Keil & Weinkauf

[57] ABSTRACT

An acylcyclohexadionethiocarboxylic S-ester of the formula

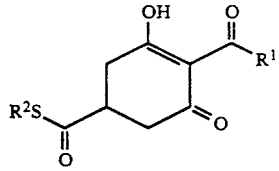

where $R^1$ and $R^2$ are substituted or unsubstituted alkyl, alkenyl, alkynyl, cycloalkyl, benzyl or phenyl, and $R^2$ is additionally hydrogen, are prepared by reacting an acylcyclohexadione II

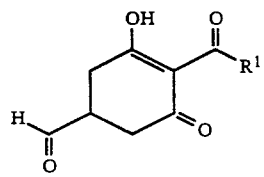

with hydroxylamine or hydroxylamine-O-sulfonic acid in an inert solvent at from 0° to 150° C., to give an acylcyclohexadione compound III

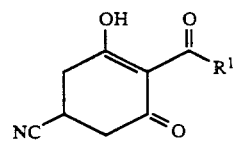

and then reacting the compound III with a mercaptan IV $$R^2\text{—SH} \qquad \qquad \text{IV}$$

in the presence of an anhydrous acid HX to give an acylcyclohexadionethiocarboximidic S-ester salt V

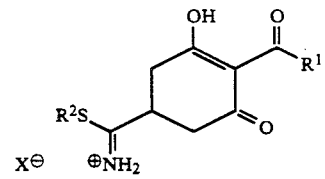

where X is the anion of the acid, and hydrolyzing the compounds V to the acylcyclohexadionethiocarboxylic S-ester I.

8 Claims, No Drawings

PREPARATION OF ACYLCYCLOHEXADIONETHIOCARBOXYLIC S-ESTERS

The present invention relates to the preparation of acylcyclohexadionethiocarboxylic S-esters of the formula I

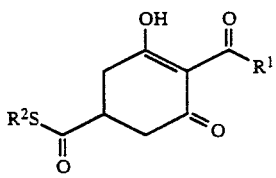

where $R^1$ is $C_1$-$C_{20}$-alkyl, $C_2$-$C_{20}$-alkenyl, $C_2$-$C_{20}$-alkynyl or $C_3$-$C_6$-cycloalkynyl each of which is unsubstituted or substituted by halogen, $C_1$-$C_4$-alkoxy or $C_1$-$C_4$-alkylthio, or is benzyl or phenyl, each of which is unsubstituted or substituted by halogen, cyano, $C_1$-$C_4$-alkyl, $C_1$-$C_4$-alkoxy, $C_1$-$C_4$-haloalkyl or nitro, and $R^2$ is hydrogen, $C_1$-$C_6$-alkyl, $C_2$-$C_6$-alkenyl, $C_2$-$C_6$-alkynyl or $C_3$-$C_6$-cycloalkyl, each of which is unsubstituted or substituted by $C_1$-$C_4$-alkoxy, $C_1$-$C_4$-alkylthio, $C_1$-$C_4$-dialkylamino, hydroxyl or halogen; benzyl or phenyl, each of which is unsubstituted or substituted by halogen, cyano, $C_1$-$C_4$-alkyl, $C_1$-$C_4$-alkoxy or nitro.

Furthermore, novel intermediates are made available by the present invention.

Acylcyclohexadionethiocarboxylic S-esters I are highly active bioregulators, as is disclosed in EP-A 293 817. There are various possibilities for the preparation of S-esters. Some methods are described below.

Route A:
S-exters are prepared from activated carboxylic acids with thiols. Examples of suitable activating reagents are diphenylphosphinic chloride (Monatsh. Chem. 110, (1979) 759), diethyl cyanophosphate (Tetrahedron Lett. 1973, 1595), carbonyl-bis-imidazolide and carbonyl-bis-triazolide (Angew. Chem. 89 (1977) 251; J. Am. Chem. Soc. 93 (1971) 1419).

Route B:
S-esters are prepared from carbonyl halides or carboxylic anhydrides or esters with thiols or thiolates in the presence or absence of a base (Houben-Weyl, Methoden der organischen Chemie, Vol. 9, pages 753-760, 1955).

Route C:
S-esters are prepared by free-radical substitution on aldehydes with organic disulfides catalyzed by UV light or with free radical initiators such as azobisisobutyronitrile (Bull. Chem. Soc. Jpn. 53, (1980), 1982).

All of these processes have one or more serious disadvantages. The activating reagents used in route A are costly or difficult to obtain, which rules out commercial utilization. The aldehyde component is used in large excess or as solvent in route C, which makes the process uneconomic for costly aldehydes.

Route B, the reaction with acid halides or anhydrides, is a standard method for preparing S-esters. However, there is a risk with the cyclohexadiones that the conventional halogenating agents such as thionyl chloride, phosphorus oxychloride, sulfuryl chloride, oxalyl chloride or phosgene will also replace the vinylic OH group by halogen, e.g. chlorine or bromine.

It is also known from the literature that adducts are formed between mercaptans and nitriles in the presence of hydrogen chloride. The resulting thiocarboximidic S-esters can be hydrolyzed to thiocarboxylic S-esters (A. Pinner, Die Iminoether, p. 80 Verlag R. Oppenheim, Berlin 1892). However, because of the competing hydrolysis to carboxamides and carboxylic acids, in general, yields of only about 10 to 25% are obtained (see, for example, U.S. Pat. No. 2,458,075 (1946) Philipps Petrol Co., inventor: Ch. M. Himel, CA 43 (1949) 3444 or Ber. Dt. Chem. Ges. 69 (1936) 2352), for which reason this sequence of reactions is not regarded as being of preparative significance (Houben-Weyl, Methoden der organischen Chemie, E5/1 p. 876, 1985).

It is an object of the present invention to find a process for preparing the acylcyclohexadionethiocarboxylic S-esters I, which are defined in the first paragraph, which is straightforward and can be carried out on an industrial scale, gives good yields of the desired product I and requires few process stages.

We have found that this object is achieved by a process for preparing acylcyclohexadionethiocarboxylic S-esters of the formula I

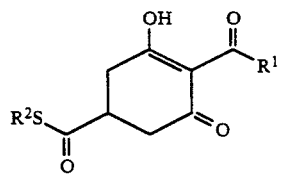

where
$R^1$ is $C_1$-$C_{20}$-alkyl, $C_2$-$C_{20}$-alkenyl, $C_2$-$C_{20}$-alkynyl or $C_3$-$C_6$-cycloalkyl, each of which is unsubstituted or substituted by halogen, $C_1$-$C_4$-alkoxy or $C_1$-$C_4$-alkylthio, or is benzyl or phenyl, each of which is unsubstituted or substituted by halogen, cyano, $C_1$-$C_4$-alkyl, $C_1$-$C_4$-alkoxy, $C_1$-$C_4$-haloalkyl or nitro, and $R^2$ is hydrogen, $C_1$-$C_6$-alkyl, $C_2$-$C_6$-alkenyl, $C_2$-$C_6$-alkynyl or $C_3$-$C_6$-cycloalkyl, each of which is unsubstituted or substituted by $C_1$-$C_4$-alkoxy, $C_1$-$C_4$-alkylthio, $C_1$-$C_4$-dialkylamino, hydroxyl or halogen; benzyl or phenyl, each of which is unsubstituted or substituted by halogen, cyano, $C_1$-$C_4$-alkyl, $C_1$-$C_4$-alkoxy or nitro, which comprises reacting, in a first stage, a compound of the formula II

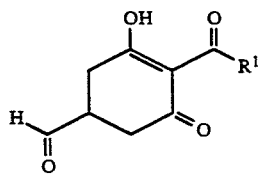

where $R^1$ has the abovementioned meaning, with hydroxylamine or hydroxylamine-O-sulfonic acid in an inert solvent at from 0° to 150° C. to give a compound of the formula III

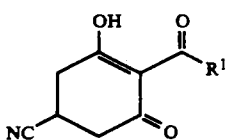
III where R¹ has the abovementioned meaning, and then, in a second stage, reacting this cyano compound of the formula III with a mercaptan of the formula IV $$R^2-SH \qquad IV$$

where R² has the abovementioned meaning, in the presence of an acid HX, to give a compound of the formula V

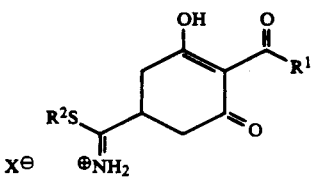
V where R¹ and R² have the abovementioned meanings, and X is the anion of an acid, and, in a third stage, hydrolyzing the compound of the formula V to give the compound of the formula I.

The reaction sequence in the process according to the invention is shown in the scheme below, where R¹ is methyl, R² is ethyl and the acid used in the second stage is hydrogen chloride.

Reaction scheme:

Reaction scheme:

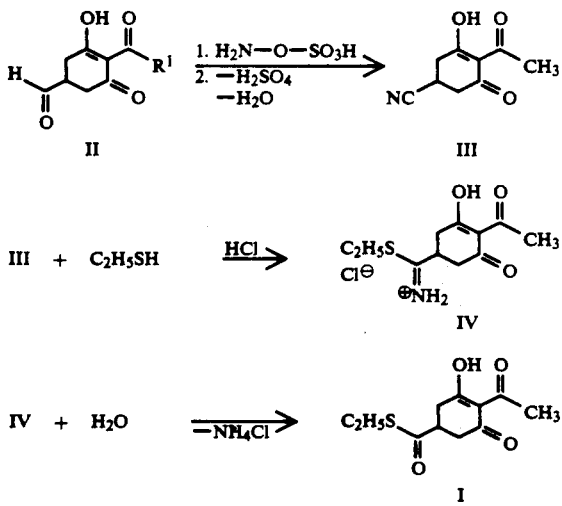

In the first stage, the formyl compound II, which can be obtained as described in DE-A-233,568, is reacted with hydroxylamine-O-sulfonic acid or hydroxylamine under condensation conditions in an inert solvent at from 0° to 150° C., in particular 20° to 80° C. It has proven particularly beneficial to carry out the reaction with hydroxyl-amine-O-sulfonic acid in water, e.g. in from 1 to 100 parts by weight of water based on the formyl compound II.

The reaction can be carried out in homogeneous or heterogeneous aqueous phase, with or without the addition of a buffer, the pH generally being from 1 to 9, in particular from 3 to 8.

The procedure is expediently such that the formyl compound II is suspended or induced to dissolve, by adding a water-miscible organic solvent, e.g. methanol or ethanol, in water. It is also possible to dissolve the starting material II in water-immiscible solvents such as ethers, e.g. diethyl ether, chlorohydrocarbons such as methylene chloride, chloroform or dichloroethane, esters such as ethyl acetate, or aromatic compounds such as benzene, toluene or xylenes. The hydroxylamine-O-sulfonic acid is added in solid form or as aqueous solution to the mixture of solvent and starting material II.

If the reaction is carried out in heterogeneous phase, it is advantageous to ensure that the phases are thoroughly mixed.

In order to achieve complete conversion into the cyano compound III, it is advisable to employ the reactants in equimolar amounts. It may be advisable, for technical reasons, to employ the formyl compound II or the hydroxylamine-O-sulfonic acid in an excess of, for example, from 1 to 100 mol %. It is preferable to use the hydroxylamine-O-sulfonic acid in an excess of from 10 to 20 mol %.

As a rule, the reaction goes to completion at up to 60° C., in particular from 20° to 40° C.

It may be advantageous in some cases to increase the reaction rate by adding catalytic amounts of a base.

Examples of suitable bases are alkali metal hydroxides such as NaOH or KOH, ammonium hydroxide, alkaline earth metal hydroxides such as magnesium hydroxide or calcium hydroxide, alkali metal carbonates or bicarbonates such as potassium carbonate or sodium bicarbonate. It is normally possible to use, based on the starting material II, from 0 to 3 equivalents of base.

The reaction can be carried out under atmospheric pressure or elevated or reduced pressure, continuously or batchwise, using the conventional techniques.

The cyanocyclohexenone compound III can be isolated from the crude reaction mixture in a conventional manner, e.g. by extraction or filtration.

It is also possible to react the starting material II with hydroxylamine in place of hydroxylamine-O-sulfonic acid, and then to eliminate water in a conventional manner, e.g. by heating with acetic anhydride or thionyl chloride at from about 80° to 150° C.

In the second stage, the acylcyclohexadione III is reacted with a mercaptan R²-SH IV in the presence of anhydrous acid and with exclusion of water. Examples of such acids are hydrogen chloride, hydrogen bromide, sulfuric acid, perchloric acid or tetrafluoroboric acid or strong carboxylic acids such as trifluoroacetic acid. Particular preference is given to hydrogen bromide and, in particular, hydrogen chloride.

In order to achieve complete conversion, it is advisable to employ the mercaptan IV and the cyano compound III in equimolar amounts. It may be advantageous, for technical reasons, to employ one of the two components in excess. The mercaptan is preferably used in an excess of from 0 to 200 mol %, preferably from 5 to 100 mol %.

Preferred R² radicals in the mercaptan are: methyl, ethyl, propyl, i-propyl, t-butyl, n-hexyl, allyl, butenyl, methoxyethyl, 3-chloropropyl, 2-dimethylaminoethyl, 2-hydroxyethyl, cyclohexyl, benzyl, 4-methylbenzyl, 4-chlorobenzyl, phenyl, p-tolyl, 4-chlorophenyl, 4-methoxyphenyl, 3-nitrophenyl.

The reaction of the cyanocyclohexadione compound III with the mercaptan IV is expediently carried out in an aprotic organic diluent. Suitable examples are ethers such as diethyl ether, tetrahydrofuran and dioxane, hydrocarbons such as pentane, hexane, cyclohexane, petroleum ether benzene and toluene, halohydrocarbons such as methylene chloride, chloroform, tetrachloromethane and 1,2-dichloroethane.

The reaction can be carried out at from −20° C. to 100° C., preferably from 0° C. to +40° C., under atmospheric pressure or elevated or reduced pressure, using the conventional techniques.

The reaction is expediently carried out in such a way that the cyanocyclohexadione compound III is introduced together with the mercaptan IV into the diluent, substantially excluding water, and the acid is added dropwise or passed in as gas at low temperature, e.g. 0° C. It is then possible, to complete the reaction, to warm to from 20° to 40° C., for example.

The carboximidic S-ester salt V, which generally separates out as crystals or an oil, can be isolated in a conventional manner, e.g. by filtration or extraction. If there is no interest in isolating the intermediates V, these can be converted by aqueous extraction, with simultaneous hydrolysis, into the final products I.

The intermediates V can be hydrolyzed in water, preferably in the presence of an acid or, in particular, in dilute aqueous mineral acid, e.g. hydrochloric, sulfuric or phosphoric acid, or dilute carboxylic acids such as acetic or formic acid.

The amount of acid is not particularly critical and is generally from 0 to 100 parts by weight of acid based on V. The acid concentration is from 0 to 20% by weight, and aqueous solutions containing from 0 to 10% by weight of acid are preferably used. The pH of the reaction mixture is preferably from 1 to 7, in particular below 2.

The reaction temperatures are likewise not critical and are usually from 0° to 100° C., in particular from 10 to 40° C.

Because the S-esters of the formula I are not soluble in water (solubility 100 mg/l), they are produced in the hydrolysis of V as an oil or solid. The hydrolysis can take place in a two-phase system by adding a water-immiscible solvent such as an ether, e.g. diethyl ether, ester, e.g. ethyl acetate, chlorohydrocarbon, e.g. methylene chloride, chloroform, tetrachloromethane or dichloroethane, aromatic hydrocarbon, e.g. benzene, toluene or xylene, which has the advantageous result that the reaction product I can be isolated directly from the organic phase. It is, of course, also possible to add the organic solvent only after the hydrolysis has taken place, in order to isolate I.

Otherwise, the process, which can also be carried out as a one-pot process without isolation of the intermediates III and V described, involves no special technical procedures.

The invention provides novel intermediates V.

The acylcyclohexadionecarboximidic S-ester salts V have the following formula

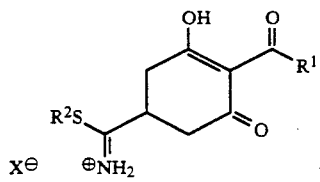

where
R$^1$ is C$_1$-C$_{20}$-alkyl, C$_2$-C$_{20}$-alkenyl, C$_2$-C$_{20}$-alkynyl or C$_3$-C$_6$-cycloalkyl, each of which is unsubstituted or substituted by halogen, C$_1$-C$_4$-alkoxy or C$_1$-C$_4$-alkylthio, or is benzyl or phenyl, each of which is unsubstituted or substituted by halogen, cyano, C$_1$-C$_4$-alkyl, C$_1$-C$_4$-alkoxy, C$_1$-C$_4$-haloalkyl or nitro;

R$^2$ is hydrogen, C$_1$-C$_6$-alkyl, C$_2$-C$_6$-alkenyl, C$_2$-C$_6$-alkynyl or C$_3$-C$_6$-cycloalkyl, each of which is unsubstituted or substituted by C$_1$-C$_4$-alkoxy, C$_1$-C$_4$-alkylthio, C$_1$-C$_4$-dialkylamino, hydroxyl or halogen; benzyl or phenyl, each of which is unsubstituted or substituted by halogen, cyano, C$_1$-C$_4$-alkyl, C$_1$-C$_4$-alkoxy or nitro, and X is a chloride, bromide, sulfate, phosphate, tetrafluoroborate, perchlorate or trifluoroacetate ion.

With a view to the biological activity of the final products I, R$^1$, R$^2$ and X in the formula V have the following preferred meanings:

R$^1$
C$_1$-C$_6$-alkyl such as methyl, ethyl, propyl, isopropyl, n-butyl, iso-butyl, s-butyl, t-butyl, n-pentyl, n-hexyl C$_3$-C$_6$-cycloalkyl such as cyclopropyl, cyclopentyl, cyclohexyl C$_2$-C$_6$-alkoxyalkyl e.g. C$_1$-C$_4$-alkoxy-C$_1$-C$_4$-alkyl such as methoxymethyl, ethoxymethyl, propyloxymethyl, 2-methoxyethyl, 2-ethoxyethyl, 2-propyloxyethyl, methoxypropyl, ethoxypropyl, C$_2$-C$_6$-alkylthioalkyl, e.g. methylthiomethyl, ethylthiomethyl, methylthioethyl, ethylthioethyl, methylthiopropyl, ethylthiopropyl, benzyl or phenyl, it being possible for the aromatic nuclei to be substituted from once to three times by halogen such as chlorine, bromine or fluorine, by cyano, nitro, C$_1$-C$_4$-alkyl such as methyl, ethyl, propyl or butyl, C$_1$-C$_4$-alkoxy such as methoxy, ethoxy, propoxy or butoxy, C$_1$-C$_4$-haloalkyl such as trifluoromethyl, difluorochloromethyl, difluoromethyl, trichloromethyl or tetrafluoroethyl, R$^2$
C$_1$-C$_6$-alkyl such as methyl, ethyl, propyl, isopropyl, n-butyl, iso-butyl, sec.-butyl, n-pentyl or n-hexyl, C$_3$-C$_5$-alkenyl such as allyl, 2-butenyl, 3-butenyl or 2-pentenyl, C$_3$-C$_4$-alkynyl such as propargyl, 2-butynyl or 3-butynyl, C$_3$-C$_6$-cycloalkyl as specified for R$^1$, C$_2$-C$_6$-alkoxyalkyl or alkylthioalkyl, in each case as specified for R$^1$, phenyl or benzyl, it being possible for the aromatic nuclei to be substituted as specified for R$^1$, chloride or bromide.

It is particularly preferred for R$^1$ to be C$_1$-C$_4$-alkyl, C$_3$-C$_6$-cycloalkyl or phenyl, R$^2$ to be C$_1$-C$_6$-alkyl, $C_3$–$C_4$-alkenyl, $C_3$–$C_4$-alkynyl, $C_2$–$C_6$-alkoxyalkyl or benzyl, and X to be chloride.

EXAMPLE 1.1

3,5-Dioxo-4-acetylcyclohexanecarbonitrile 19.3 g (0.11 mol) of 5-formyl-2-acetylcyclohexane-1,3-dione were introduced into 200 ml of distilled water and, at room temperature, 14.7 g (0.13 mol) of hydroxylamine-O-sulfonic acid were added. The mixture was then stirred at room temperature for 17 h. The precipitate was filtered off with suction, washed with water and dried. 11.5 g (61% of theory) of 3,5-dioxo-4-acetylcyclohexanecarbonitrile were obtained (melting point 94 to 97° C.).

EXAMPLE 1.2

3,5-Dioxo-4-propionylcyclohexanecarbonitrile 30.7 g (0.16 mol) of 5-formyl-2-propionylcyclohexane-1,3-dione were introduced into 150 ml of distilled water and, at room temperature, 21.0 g (0.19 mol) of hydroxylamine-O-sulfonic acid were added. The mixture was then stirred at room temperature overnight. The precipitate was filtered off with suction, washed with water and dried. 23.8 g (71% of theory) of 3,5-dioxo-4-propionylcyclohexanecarbonitrile were obtained (melting point 70° to 74° C.).

EXAMPLE 1.5

3,5-Dioxo-4-palmitoylcyclohexanecarbonitrile 43 g (0.12 mol) of 5-formyl-2-palmitoylcyclohexane-1,3-dione were suspended in 150 ml of distilled water. To this were added 15.7 g (0.14 mol) of hydroxylamine-O-sulfonic acid dissolved in 50 ml of water. The heterogeneous reaction mixture was stirred at room temperature overnight. The resulting solid was filtered off with suction, washed with water and dried. 37.7 g (86% of theory) of 3,5-dioxo-4-palmitoylcyclohexanecarbonitrile were isolated (melting point 66° to 69° C.).

The cyclohexenone compounds III shown in Table 1 can be prepared in a similar manner.

TABLE 1

Cyclohexenone compounds III

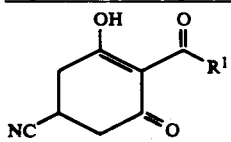

III

| No. | $R^1$ | m.p. [°C.] | phys. data $^1$H-NMR [δ in ppm] |
|---|---|---|---|
| 1.1 | methyl | 94 to 97 | |
| 1.2 | ethyl | 70 to 74 | |
| 1.3 | propyl | 47 to 50 | |
| 1.4 | butyl | 58 to 59 | |
| 1.5 | pentadecanyl | 66 to 69 | |
| 1.6 | cyclopropyl | | 1.2(m); 1.35(m); 3.0(m); 3.3(m) |
| 1.7 | cyclohexyl | | |
| 1.8 | phenyl | | |
| 1.9 | 4-Cl, 2-$NO_2$—$C_6H_3$ | 184 to 187 (decomposition) | |

EXAMPLE 2.1

S-Methyl 3,5-dioxo-4-propionylcyclohexanethiocarboximidate hydrochloride 5.0 g (0.026 mol) of 3,5-dioxo-4-propionylcyclohexanecarbonitrile and 1.37 g (0.028 mol) of methyl mercaptan were dissolved in 100 ml of dry diethyl ether. The solution was cooled to 0° C. and then a vigorous stream of dry hydrogen chloride was passed through it. After 0.5 h the gas stream was turned off, and the reaction mixture was slowly warmed to room temperature. It was again cooled to 0° C., hydrogen chloride was passed in (0.5 h) and then the cooling was removed and the mixture was left to stand overnight. The crystals which formed were filtered off with suction and dried in vacuo: 5.4 g (74% of theory) of compound 2.1 [melting point 161° C. (decomposition)].

EXAMPLE 2.2

S-Ethyl 3,5-dioxo-4-propionylcyclohexanethiocarboximidate hydrochloride 19.3 g (0.1 mol) of 3,5-dioxo-4-propionylcyclohexanecarbonitrile and 6.5 g (0.105 mol) of ethyl mercaptan were dissolved in 800 ml of dry diethyl ether and reacted with hydrogen chloride as described in Example 2.1: 20.7 g (71% of theory) of compound 2.2 [melting point 180°–185° C. (decomposition)].

EXAMPLE 2.3

S-Ethyl 3,5-dioxo-4-palmitoylcyclohexanethiocarboximidate hydrochloride 7.5 g (0.02 mol) of 3,5-dioxo-4-palmitoylcyclohexanecarbonitrile and 1.86 g (0.03 mol) of ethylmercaptan were suspended in 150 ml of dry diethyl ether. The suspension was cooled to 0° C. and then a vigorous stream of dry (concentrated sulfuric acid) hydrogen chloride was passed through it. After 0.5 h the stream of gas was turned off, and the reaction mixture was slowly warmed to room temperature. It was again cooled to 0° C., hydrogen chloride was passed in, the cooling was removed and, after a total of 6 h, the solid was filtered off, washed with ether and dried: 7.3 g (77% of theory) of compound 2.3 [melting point 65°–68° C. (decomposition)].

The carboximidic S-esters V listed in Table 2 can be prepared in a similar manner.

TABLE 2

Acylcyclohexadionethiocarboximidic S-esters V

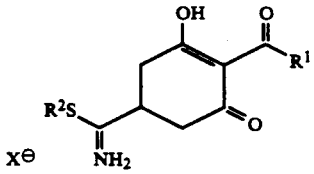

V

| No. | $R^1$ | $R^2$ | X | phys. data m.p. (°C.) |
|---|---|---|---|---|
| 2.1 | ethyl | methyl | Cl | 161 (decomp.) |
| 2.2 | ethyl | ethyl | Cl | 180 to 185 (decomp.) |
| 2.3 | palmitoyl | ethyl | Cl | 65–68 |
| 2.4 | methyl | ethyl | Cl | 160 to 165 (decomp.) |
| 2.5 | ethyl | 2-methoxyethyl | Cl | oil |
| 2.6 | cyclopropyl | 2-methoxyethy | Cl | oil |

EXAMPLE 3.1

S-Methyl-3,5-dioxo-4-propionylcyclohexanethiocarboxylate 2.8 g (0.01 mol) of compound 2.1 were dissolved in 50 ml of 10% strength hydrochloric acid and stirred at room temperature overnight. The white precipitate was filtered off, washed with water and dried under reduced pressure: 1.95 g (80% of theory) of compound 3.1 (melting point 81° C.).

EXAMPLE 3.2

S-Ethyl 3,5-dioxo-4-propionylcyclohexanethiocarboxylate 5.8 g (0.02 mol) of compound 2.2 were dissolved in 100 ml of 10% strength hydrochloric acid and stirred at room temperature overnight. The white precipitate was filtered off, washed with water and dried under reduced pressure: 4.1 g (80% of theory) of compound 3.2 (melting point 70° C.).

EXAMPLE 3.3

S-Ethyl 3,5-dioxo-4-palmitoylcyclohexanethiocarboxylate 3.0 g (6.3 mmol) of compound 2.3 were suspended in 50 ml of water and stirred vigorously at room temperature overnight. The solid was filtered off, washed with water and dried under reduced pressure: 2.4 g (86% of theory) of compound 3.3 (melting point 56°–58° C.).

The compounds I listed in Table 3 which follows were prepared in a similar manner.

TABLE 3

Cyclohexanethiocarboxylic S-esters I

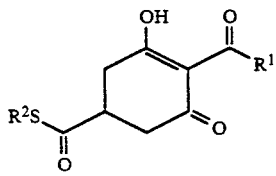

| No. | $R^1$ | $R^2$ | phys. data, m.p. (°C.) |
|---|---|---|---|
| 3.1 | ethyl | methyl | 81 |
| 3.2 | ethyl | ethyl | 70 |
| 3.3 | palmitoyl | ethyl | 56 to 58 |
| 3.4 | methyl | ethyl | |
| 3.5 | ethyl | 2-methoxyethyl | oil |
| 3.6 | cyclopropyl | ethyl | oil |
| 3.7 | cyclopropyl | 2-methoxyethyl | oil |
| 3.8 | 4-Cl, 2-$NO_2$—$C_6H_3$ | Ethyl | oil |

We claim:

1. A process for preparing an acylcyclohexadionethiocarboxylic S-ester of the formula I

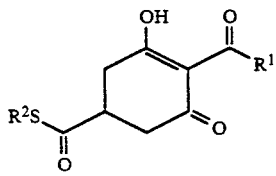

where $R^1$ is $C_1$-$C_{20}$-alkyl, $C_2$-$C_{20}$-alkenyl, $C_2$-$C_{20}$-alkynyl or $C_3$-$C_6$-cycloalkyl, each of which is unsubstituted or substituted by halogen, $C_1$-$C_4$-alkoxy or $C_1$-$C_4$-alkylthio, or is benzyl or phenyl, each of which is unsubstituted or substituted by halogen, cyano, $C_1$-$C_4$-alkyl, $C_1$-$C_4$-alkoxy, $C_1$-$C_4$-haloalkyl or nitro, and $R^2$ is hydrogen, $C_1$-$C_6$-alkyl, $C_2$-$C_6$-alkenyl, $C_2$-$C_6$-alkynyl or $C_3$-$C_6$-cycloalkyl, each of which is unsubstituted or substituted by $C_1$-$C_4$-alkoxy, $C_1$-$C_4$-alkylthio, $C_1$-$C_4$-dialkylamino, hydroxyl or halogen; benzyl or phenyl, each of which is unsubstituted or substituted by halogen, cyano, $C_1$-$C_4$-alkyl, $C_1$-$C_4$-alkoxy or nitro, which comprises reacting, in a first stage, a compound of the formula II

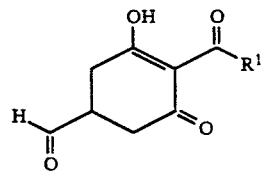

where $R^1$ has the abovementioned meaning, with hydroxylamine or hydroxylamine-O-sulfonic acid in an inert solvent at from 0° to 150° C. to give a compound of the formula III

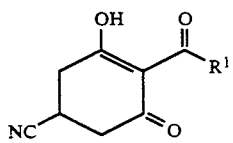

where $R^1$ has the abovementioned meaning, and then, in a second stage, reacting this cyano compound of the formula III with a mercaptan of the formula IV $$R^2-SH \qquad IV$$

where $R^2$ has the abovementioned meaning, in the presence of an anhydrous acid HX, to give a compound of the formula V

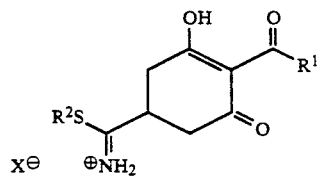

where $R^1$ and $R^2$ have the abovementioned meanings, and X is the anion of an acid, and, in a third stage, hydrolyzing the compound of the formula V to give the compound of the formula I.

2. The process of claim 1, in the first stage of which compound I is reacted with hydroxylamine-O-sulfonic acid in homogeneous or heterogeneous aqueous phase at a, pH of from 1 to 9.

3. The process of claim 1, wherein the reaction with hydroxylamine-O-sulfonic acid is carried out at a pH of from 3 to 8.

4. The process of claim 1, wherein the reaction in the first stage is carried out at from 20° to 80° C.

5. The process of claim 1, wherein the acid used in the second stage is hydrogen chloride or hydrogen bromide.

6. The process of claim 1, wherein the reaction in the second stag is carried out at from −20° to 100° C.

7. The process of claim 1, wherein the hydrolysis of compound V is carried out at a pH of from 1 to 7 and at from 0° to 100° C.

8. The process of claim 1, wherein stages 1 to 3 are carried out without isolation of the intermediates III and V.

* * * * *

UNITED STATES PATENT AND TRADEMARK OFFICE
CERTIFICATE OF CORRECTION

PATENT NO. : 5,130,453
DATED     : July 14, 1992
INVENTOR(S) : Juergen KAST et al.

It is certified that error appears in the above-identified patent and that said Letters Patent is hereby corrected as shown below:

```
in the Abstract, column 1, bottom line:
"fomrula" should read -- formula --

Claim 2, column 10, line 60; after "a" delete ","

Claim 6, column 11, line 4: "stag" should read -- stage --
```

Signed and Sealed this

Tenth Day of August, 1993

Attest:

MICHAEL K. KIRK

*Attesting Officer*   Acting Commissioner of Patents and Trademarks